United States Patent [19]

Bush et al.

[11] Patent Number: 5,282,845
[45] Date of Patent: Feb. 1, 1994

[54] MULTIPLE ELECTRODE DEPLOYABLE LEAD

[75] Inventors: Mary E. Bush; Craig E. Mar, both of Fremont; Eric S. Fain, Menlo Park, all of Calif.

[73] Assignee: Ventritex, Inc., Sunnyvale, Calif.

[21] Appl. No.: 591,389

[22] Filed: Oct. 1, 1990

[51] Int. Cl.⁵ .............................................. A61N 1/05
[52] U.S. Cl. ..................................... 607/128; 607/127
[58] Field of Search ................... 128/784, 785, 786, 642

[56] References Cited

U.S. PATENT DOCUMENTS

| Re. 27,569 | 2/1973 | Ackerman | 128/786 |
|---|---|---|---|
| 3,749,101 | 7/1973 | Williamson | 128/419 P |
| 3,844,292 | 10/1974 | Bolduc | 128/419 P |
| 3,865,118 | 11/1975 | Bures | 128/419 P |
| 3,866,615 | 2/1975 | Hewson | 128/784 |
| 3,942,536 | 3/1976 | Mirowksi et al. | 128/419 D |
| 4,112,952 | 9/1978 | Thomas et al. | 128/419 P |
| 4,289,138 | 9/1981 | Halvorsen | 128/642 |
| 4,291,707 | 9/1981 | Heilman et al. | 128/784 |
| 4,355,642 | 10/1982 | Alferness | 128/642 |
| 4,355,646 | 10/1982 | Kallok et al. | 128/786 |
| 4,402,330 | 9/1983 | Lindemans | 128/786 |
| 4,522,212 | 6/1985 | Gelinas et al. | 128/642 |
| 4,567,900 | 2/1986 | Moore | 128/784 |
| 4,574,814 | 3/1986 | Buffet | 128/786 |
| 4,603,705 | 8/1986 | Speicher et al. | 128/786 |
| 4,662,377 | 5/1987 | Heilman et al. | 128/419 D |
| 4,679,572 | 7/1987 | Baker, Jr. | 128/786 |
| 4,699,147 | 10/1987 | Chilson et al. | 128/642 |
| 4,708,145 | 11/1987 | Tacker, Jr. et al. | 128/419 D |
| 4,774,952 | 10/1988 | Smits | 128/419 D |
| 4,860,769 | 8/1989 | Fogarty et al. | 128/786 |
| 4,862,887 | 7/1989 | Weber et al. | 128/642 |
| 4,865,037 | 9/1989 | Chin et al. | 128/419 D |

FOREIGN PATENT DOCUMENTS

| 0071495A3 | 6/1982 | European Pat. Off. . |
| 0317490A2 | 8/1988 | European Pat. Off. . |
| WO89/06148 | 7/1989 | PCT Int'l Appl. . |
| 2217993A | 8/1989 | United Kingdom . |

OTHER PUBLICATIONS

2 page article of Mansfield Scientific Inc. "Ventri-Stat Flare" Temporary Emergency Transthoracic Pacing Electrode Kit, obtained from the file history of another patent application as indicated in upper righthand corner.

Primary Examiner—William E. Kamm
Assistant Examiner—Scott M. Getzow
Attorney, Agent, or Firm—Steven M. Mitchell; Mark J. Meltzer

[57] ABSTRACT

An implantable defibrillator lead comprises a flexible, conductive lead member having proximal and distal end portions. The distal end portion defines a plurality of separate, curvilinear electrodes which naturally extend laterally outwardly in a curved arrangement from the remainder of the lead. However, by desired means, the curvilinear electrodes may be temporarily extended out straight, substantially parallel to the axis of the remainder of said lead member, to facilitate implantation of the lead. This may be preferably accomplished by a flexible sheath that encloses the lead member in longitudinally slidable relation.

33 Claims, 4 Drawing Sheets

MULTIPLE ELECTRODE DEPLOYABLE LEAD

BACKGROUND OF THE INVENTION

This invention relates to deployable leads having electrodes which may be held in a position for inserting of the lead into the body of a patient, followed by placing of the electrodes into a position of use in which they assume a different configuration. More specifically, the invention relates to the field of implantable automatic defibrillators.

Examples of deployable defibrillation electrodes are disclosed in Fogarty et al. U.S. Pat. No. 4,860,769 and Moore U.S. Pat. No. 4,567,900 and Fain et al. co-pending U.S. Pat. application Ser. No. 404,517, filed Sep. 6, 1989.

As described in Fogarty et al. it is well known in the field of cardiology that certain types of cardiac arrhythmias known as ventricular tachycardia and fibrillation can often be effectively treated by the application of electrical shocks to the heart. Such defibrillation may be achieved by the application of electrical paddles to the chest of a patient, or directly to the heart tissue, if the chest is open during surgery.

More recent improvements have lead to the development of implantable defibrillators which monitor the heart for arrythmias and automatically initiate defibrillation when an arrythmia occurs. Such devices typically incorporate electrodes which are located next to the heart, or on an intravascular catheter, or both. Because the electrodes are closer to the heart tissue, implanted defibrillators require less electrical energy to stimulate the heart than do external electrodes.

However, major surgery is generally necessary to implant the present defibrillator lead systems, for example a median sternotomy or a lateral thoracotomy. These procedures can be very traumatic to the patient, and may have significant adverse side effects. Candidates for such procedures or any procedure include only those persons for whom the potential benefits outweigh the risks. Because of the significant surgical risks of the present lead systems, many patients who might otherwise benefit from the use of an implantable defibrillator are excluded.

While leads are generally known which are collapsed into an advancement position for implantation in the body and then are deployable to an operating position inside the body, the defibrillator lead electrodes require a substantially large area, to provide even current distribution and low defibrillation energy thresholds. Thus, difficulties are encountered in the designing of deployable defibrillator electrodes.

In electrodes such as those shown in Fogarty et al., it would be of advantage if the long, spiral electrode could be reduced in length. By this improvement, the length along which the electrode has to deploy is shorter and more controllable, and electrical resistance can be minimized. Similarly in the Moore patent, the size of the electrode, when distorted into shape for movement through a catheter as shown therein may be unduly large.

In accordance with this invention, a lead carrying multiple electrodes is provided to achieve a desired length reduction of the electrodes, as well as other significant advantages over electrodes of the prior art. For example, a multiple electrode system provides more redundance to the system so that it can continue to operate in the event of failure of one of the electrodes. Also, the lead of this invention may be inserted through a small incision with minimum trauma to the patient, while providing adequate electrode surface area for defibrillation, due to the deployable nature of the lead.

DESCRIPTION OF THE INVENTION

By this invention, an implantable defibrillator lead is provided. The lead comprises a flexible, conductive lead member having proximal and distal ends. The conductor of the lead member may be a coil or a multistrand cable. Means are also provided for holding the lead in a generally linear and typically straight configuration. For example, a sheath may enclose the lead in longitudinally slidable relation, whereby a distal end portion of the lead is enclosed in the sheath in a first sliding position, and the distal end portion projects from the distal end of the sheath in a second sliding position. The distal end portion defines a plurality of separate, curvilinear electrodes which collapse and straighten to fit into said sheath in the first position, and which deploy by flexing laterally outwardly in a curved arrangement from the remainder of said lead in the second position.

If desired, the sheath may be replaced by one or more stylets which communicate with each of the curvilinear electrodes to hold them straight or in any desired predetermined position until the stylets are removed. In that case also, as well as in the situation where a sheath is used, the curvilinear electrodes can be released to move laterally outwardly from the axis of the lead into operating configuration upon removal of the stylet or stylets.

The curvilinear electrodes each preferably comprise a coiled metal wire, typically close-wound, extending in a curvilinear direction, for example a spiral direction, outwardly. The coiled wire conductors are preferably free of a central member extending through the coiled wire, having its own, inherent resilience so that each electrode will naturally resume its original, curvilinear shape after being straightened in the sheath without needing a central member to provide resilience. By this means, coiled, curvilinear electrode members used in this invention can provide more positive outward springing than the electrodes of the Fogarty et al. patent, where a coiled electrode is carried on a nonmetallic, flexible, member. Also, the structure of the electrodes preferably used in this invention is more fatigue resistant than electrodes that rely on a central supporting wire for resilience.

The word "curvilinear" is intended to imply that the electrodes used in this invention extend in a curved path, referring to their general direction of extension. Each curvilinear electrode may comprise a braided cable formed of wires, or a wound coil of wire or wires or metal flat ribbon, or coaxially wound coils, with the braided or coiled array generally extending in the curvilinear direction, to define the curvilinear electrode.

Because a plurality of such curvilinear electrodes are used, they can each be substantially shorter than can the single electrode of the Fogarty et al. patent cited above, and they can be considerably less complex than the single electrode of Moore cited above.

The electrodes may comprise multifilar coils of several intercoiling strands to lower resistance, provide additional redundancy, and help the coil electrode keep its shape by increasing pitch without reducing coil density.

In one preferred embodiment, the separate, curvilinear electrodes may each define an arc having an angle of at least about 180° but less than a complete loop, i.e. not a closed, attached loop although the arc may be 360° or more. At least a pair of said separate, curvilinear electrodes defining arcs may project outwardly in opposed, transverse directions, which facilitates their free, lateral deployment at their desired site in the patient, typically near the heart, while minimizing the chances of the respective curvilinear electrodes tangling.

Alternatively, the separate, curvilinear electrodes can define a closed loop, in which both ends of the linear electrodes are attached to the lead.

Preferably, the curvilinear electrodes may comprise a platinum-iridium alloy which provides excellent physical characteristics as well as excellent electrical transmission characteristics to the electrodes. Alternatively, other alloys with good physical and electrical characteristics, such as MP35N, may be used, containing essentially 35 percent nickel, 35 percent cobalt, 20 percent chromium, and 10 percent molybdenum, by weight.

The sheath is preferably used to hold the electrodes in relatively linear relation during advancement, and then the sheath is withdrawn to permit deployment. The sheath preferably comprises an electrically insulating material such as plastic, silicone rubber, or the like. Thus the sheath may remain in position about the majority of the lead, if desired, while allowing the electrodes to be exposed distally of the sheath and to be laterally deployed.

It may also be desirable for each curvilinear electrode to have a retention member running along its length, either internally or externally, to keep the electrode intact in case of breakage. Thus, in the event of breakage or other reason, the entire system can be optionally replaced back into its installing position by advancement of the sheath or stylets, and then withdrawn from the patient for replacement with a new unit. Also or alternatively, each electrode may carry a coating of platinum, iridium oxide, or the like as a protection against corrosion, where that is deemed desirable.

It may also be desirable for the curvilinear electrodes to be staggered in the same plane to provide optimum distribution of current, and also to minimize possible tangling as the electrodes are deployed. Alternatively, the respective curvilinear electrodes may be distributed in different planes so that the deployed lead is a three dimensional structure, rather than just a substantially two dimensional structure. This provides the advantages of better fixation and stability, more uniform current distribution when used endocardially, and the avoidance of tangling.

The lead of this invention may further comprise a fixation device adjacent its distal tip. Such a fixation device may comprise a known screw-in distal tip fixation device. Alternatively, a passive fixation device may be used such as outwardly extending vanes, intended to be caught on the trabeculae within the heart to hold the lead in place.

As a further alternative, the lead of this invention may carry a pacing/sensing unit adjacent its distal end, so that the lead is useful not only for defibrillation, but also for heart pacing and sensing of heart beats.

Not only may the lead carry electrodes that are straightened by an outer sleeve that is longitudinally movable, but also a removable inner stylet may be provided to pass within tubular or spiral electrodes to straighten them. Since multiple electrodes are used, the inner stylet may be of a multiple-strand cable structure in which the strand components of the cable are separated at the distal end, each component passing into an electrode for straightening thereof. Thus the lead can be held in its insertion position using an inner stylet, and then the lead electrodes assume their natural shape upon removal of the inner stylet.

As another alternative, a removable stiffening catheter may be placed along the lead and the sheath which covers the electrodes and straightens them out during advancement. This stiffening catheter can also be used to stiffen the lead during insertion as well as straighten the electrodes, if desired.

As another advantage of this invention, each electrode typically connects to the lead conductor near the center of the area of the electrodes, taken together. Thus, the current flows radially outwardly from the center along the somewhat resistive electrodes. Therefore, current is preferentially delivered to the portion of the heart adjacent the electrode center. This avoids undesirable edge effects.

A pair of leads, at least one of which is typically made in accordance with this invention, may be implanted in or adjacent the heart in such a manner that an unbroken wall of heart tissue separates the two electrodes. Thus, even in the event of some movement of one or both of the electrodes, the respective electrodes remain separated by the wall of heart tissue.

For example, one lead may be placed in the right ventricle of the heart, and another is placed intrapericardially, i.e., outside of the heart itself but within the pericardial cavity.

Alternatively, one lead may be placed in the right ventricle of the heart, and another lead is placed extrapericardially, i.e., against the outer surface of the fibrous layer of the parietal pericardium.

As a third alternative, one lead may be placed intrapericardially, while another lead is placed extrapericardially.

As a fourth alternative, both leads may be placed extrapericardially.

As a fifth alternative, both leads may be placed intrapericardially.

The leads may extend into their positions through separate holes formed in the pericardial membrane, which provides further assistance in assuring that the leads stay separated from each other.

By these means, a pair of defibrillation leads may be safely and reliably positioned in active relation with the heart, for providing defibrillation energies when and as required.

By this invention one or more deployable electrodes may be applied to the heart for defibrillation, and, if desired, for other purposes as well, without significant surgery, by simple advancement of the electrode through a small aperture to a desired site at the heart. Then, the electrode may be deployed in the manner discussed above, with the electrode being optionally secured by some mechanical means in its desired position.

DESCRIPTION OF SPECIFIC EMBODIMENTS

Figures 1, 1A, 2A, 2B, 3, 4, 5:
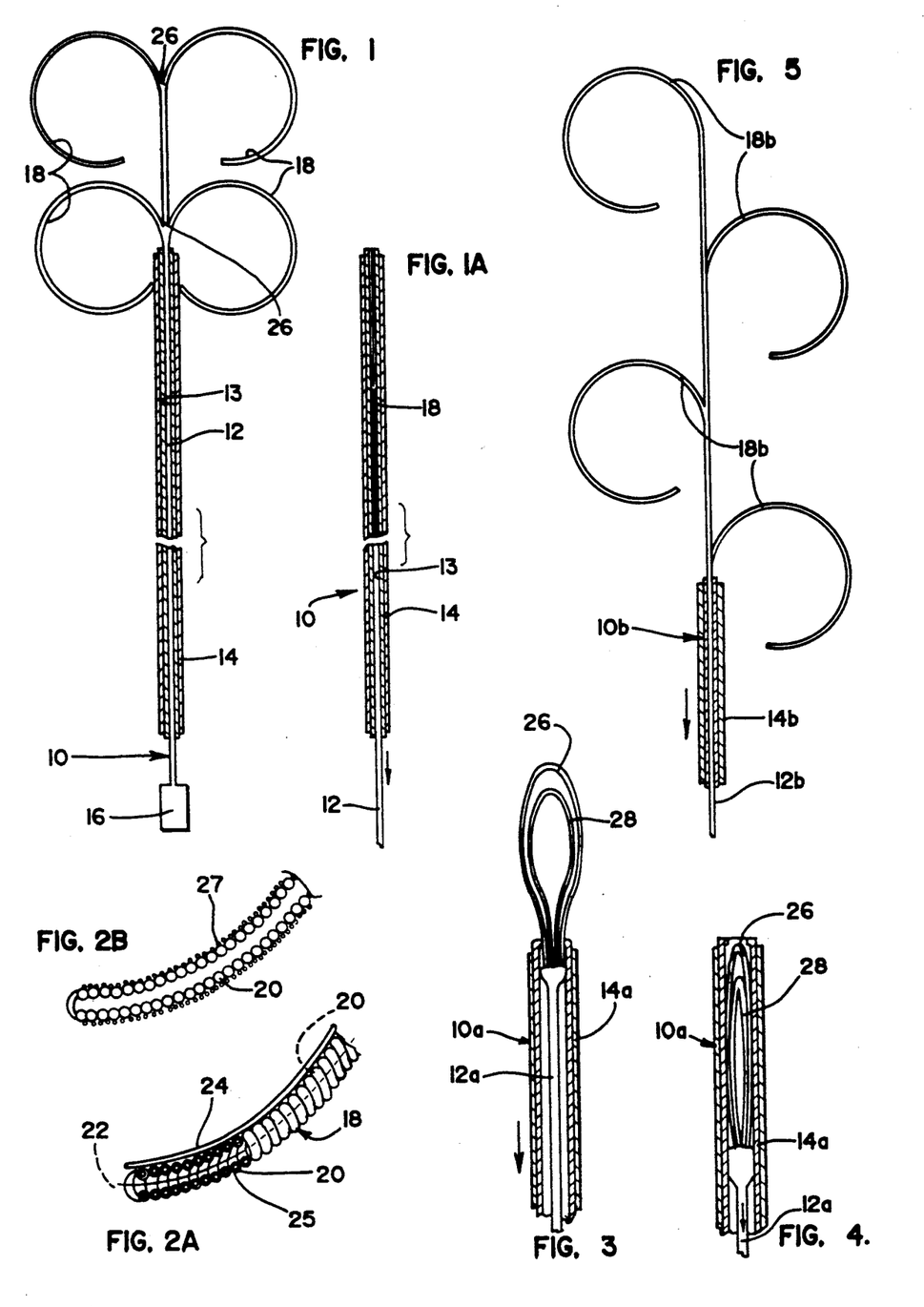
FIG. 1 is a plan view, taken partly in section, of a multiple electrode defibrillation lead in accordance with this invention, shown in its expanded, operating configuration.
FIG. 1a shows the defibrillation lead of FIG. 1 in its position for installation into the body, with the electrodes being in their first position, fitting into a sheath.
FIG. 2a is an enlarged, fragmentary, partially broken away perspective view showing a portion of one of the electrodes of the lead of FIG. 1.
FIG. 2b is a partial, enlarged sectional view of another embodiment of the electrode of the lead of FIG. 1.
FIG. 3 is a fragmentary plan view, taken partly in section, showing another embodiment of the multiple electrode defibrillator lead of this invention.
FIG. 4 is a similar plan view, taken partly in section, of the lead of FIG. 3 in its retracted, traveling position within the sheath.
FIG. 5 is a similar view of another embodiment of the multiple electrode defibrillator lead of this invention.

Referring to FIGS. 1 and 2, an implantable defibrillator lead 10 is disclosed which comprises a flexible, conductive, insulated lead member 12, the majority of which carries insulation 13 and is positionable within a sliding sheath 14. Lead 12 connects to a conventional electronic connector 16 for connecting with a system for sending energy pulses through the lead, at its proximal end. At its distal end, lead 12 defines four curvilinear electrodes 18. Each of the curvilinear electrodes 18 may comprise a coiled, conductive metal wire or ribbon 20 in which the axis 22 of the coil extends in said curvilinear direction. The coiled wire 20 preferably comprises a close-wound coil in which the individual loops thereof are in contact with each other, as shown in FIGS. 2a and 2b. The wire may comprise a platinum-iridium alloy for providing desired excellent physical characteristics to the electrode.

Additionally, electrode 18 may carry a length of polymeric material 24, such as silicone rubber, (FIG. 2a) extending along the length of each electrode 18 and adhering to the coils of wire 20 to keep the electrode intact, in case of breakage.

Also, wire 20 may carry outer coating 25 of iridium oxide or other corrosion resisting material, or the coils of wire 20 forming the coiled electrode may be coated with iridium oxide or the like, to reduce corrosion.

FIG. 2b shows a variant of electrode 18, in which the coils of wire 20, either coated with a protective agent or uncoated as may be desired, define an inner helical member, while an outer, coiled helical member 27 is also present. While coils of wire 20 may be of the same design as shown in FIG. 2a, the outer helical coil 27 may be made of platinum wire, typically of smaller diameter than the diameter of coils of wire 20, with the platinum coiled wire 27 serving as a protective aid against corrosion and the like.

The inner coil 20 can then provide improved shape memory and mechanical strength, coupled with the corrosion resistance provided by the outer coil 27.

Also, either of the electrode designs of FIGS. 2a or 2b may be multifilar in nature, i.e., several strands of coiled wire 20 are coiled together, so that adjacent loops of coil are from different strands. Typically from 2 to 4 separate strands may be provided in this circumstance. Such multifilar coils exhibit lower electrical resistance, provide additional redundancy, and help the electrode keep its shape by increasing the pitch of the individual, coiled strands without changing the coil density. "Pitch" is the distance from center to center of the wire in two turns of a wire in a coil. In short, coil density can be maximized as shown since the individual loops 20 are in contact with each other, but the pitch of the individual wires can be increased relative to axis 22.

The electrode is originally in its configuration of FIG. 1a, in which sheath 14 is advanced to enclose the respective electrodes 18 which, in turn, are forced into a configuration that is generally parallel to the axis of sheath 14. In this configuration, it is easier to advance lead 10 into the patient through a major blood vessel into a chamber of the heart. Lead 10 may also penetrate through a hole cut or punched in the parietal pericardium in a desired position, to enter the pericardial cavity.

Figure 12:
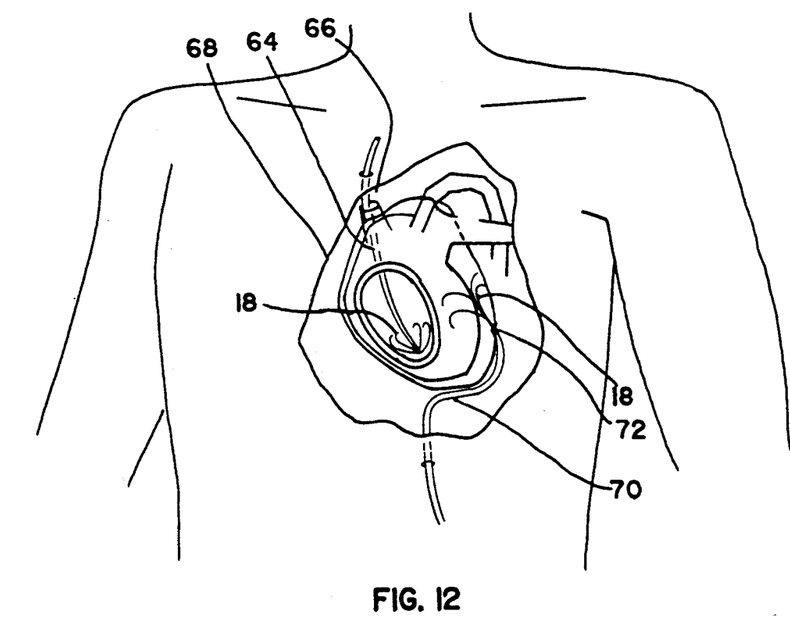
FIG. 12 is a schematic view of the human heart of a patient, illustrating the implantation of a pair of the multiple electrode leads of this invention.

Then, as shown in FIG. 1, and also as broadly shown in FIG. 12, sheath 14 may be retracted relative to electrodes 18, permitting them to assume a natural configuration by their natural resilience, moving laterally outwardly in a curved arrangement from the remainder of said lead.

The curvilinear shape of electrodes 18 may be of the form of a circle or a spiral, although in the FIG. 1 embodiment a complete, closed circle or spiral is not defined by any of the electrodes 18. The junction point 26 of each of electrodes 18 with the remainder of lead 12 may be at a position which is the radially inward most position of the electrode spiral as defined, with the remainder of each electrode 18 spiralling radially outwardly. In this manner, the current flow starts at an inner point of the spiral path of each of the somewhat resistive curvilinear electrodes 18 and moves laterally outwardly, to avoid undesirable edge effects as described above.

Thus, it can be seen that the lead of FIGS. 1-3 provides significant advantages over the leads of the prior art. A substantial amount of electrode area is provided among the four electrodes 18 over a relatively short length of the lead. Also, since each electrode 18 is relatively short in length, they do not extend outwardly from the axis of the lead by an undue distance, and thus are more easily spontaneously deployable within or adjacent the heart. Likewise, their deployable characteristic is of great advantage for the reasons discussed above, while a substantial surface area for the electrodes is provided.

Also, in the event of a failure of one of the electrodes 18, it may not be necessary to remove the lead, since the three other electrodes 18 will still be operable. Likewise, the overall resistance of the system is reduced, since each of the electrodes 18 connect directly with lead 12, and are shorter in length than would be expected from the viewpoint of the prior art for a single defibrillation electrode of equivalent capacity.

FIGS. 3 and 4 disclose an alternative embodiment in accordance with this invention. In this embodiment, a portion of lead 10a is shown, in which conductive lead member 12a is similar to lead member 12 and is terminated at its distal end with a pair of loop electrodes 26, 28. If desired, one of the loop electrodes 28 may be positioned within the other of the loop electrodes 26. Both ends of each of the electrodes 26, 28 communicate with lead member 12a.

Sheath 14a may be of similar structure and function to sheath 14 of the previous embodiment. In FIG. 4, the defibrillator lead is shown in its position to be advanced into the body to its final site of implantation. Then, when the site is released, sheath 14a is pulled backwards to deploy electrodes 26, 28 by their natural springing memory as may be desired.

As one particular embodiment, electrode 26 may, by its natural springing nature, move upwardly out of the plane of the drawing, while inner electrode 28 moves downwardly out of the plane of the drawing, so that the two electrodes occupy a three dimensional configuration.

Otherwise, the embodiment of FIGS. 3 and 4 is substantially similar in its structure and operation to the previous embodiment.

Referring to FIG. 5, defibrillator lead 10b is disclosed. As before, a conductive lead member 12b, with its distal end as shown, is enclosable within sheath 14b. As before, four electrodes 18b are shown, similar in nature to electrodes 18 of the embodiment of FIGS. 1-2. However, in this embodiment, electrodes 18b are staggered along the longitudinal dimension in a manner that is different from the electrodes 18 of FIG. 1, which are in pairs, although opposed to each other. This staggered arrangement of electrodes 18b provides an advantage that there is less opportunity for tangling of the electrodes as sheath 14b is pulled in the proximal direction to allow curvilinear electrodes 18b to flex laterally outwardly into their normal, curved arrangement as shown in FIG. 5. This particular embodiment can be used when it is acceptable to have an electrode arrangement that is of greater longitudinal extent than in the embodiment of FIG. 1. Otherwise, the embodiment of FIG. 5 is similar in structure and function to the embodiment of FIGS. 1-2.

Figures 6, 7, 8:
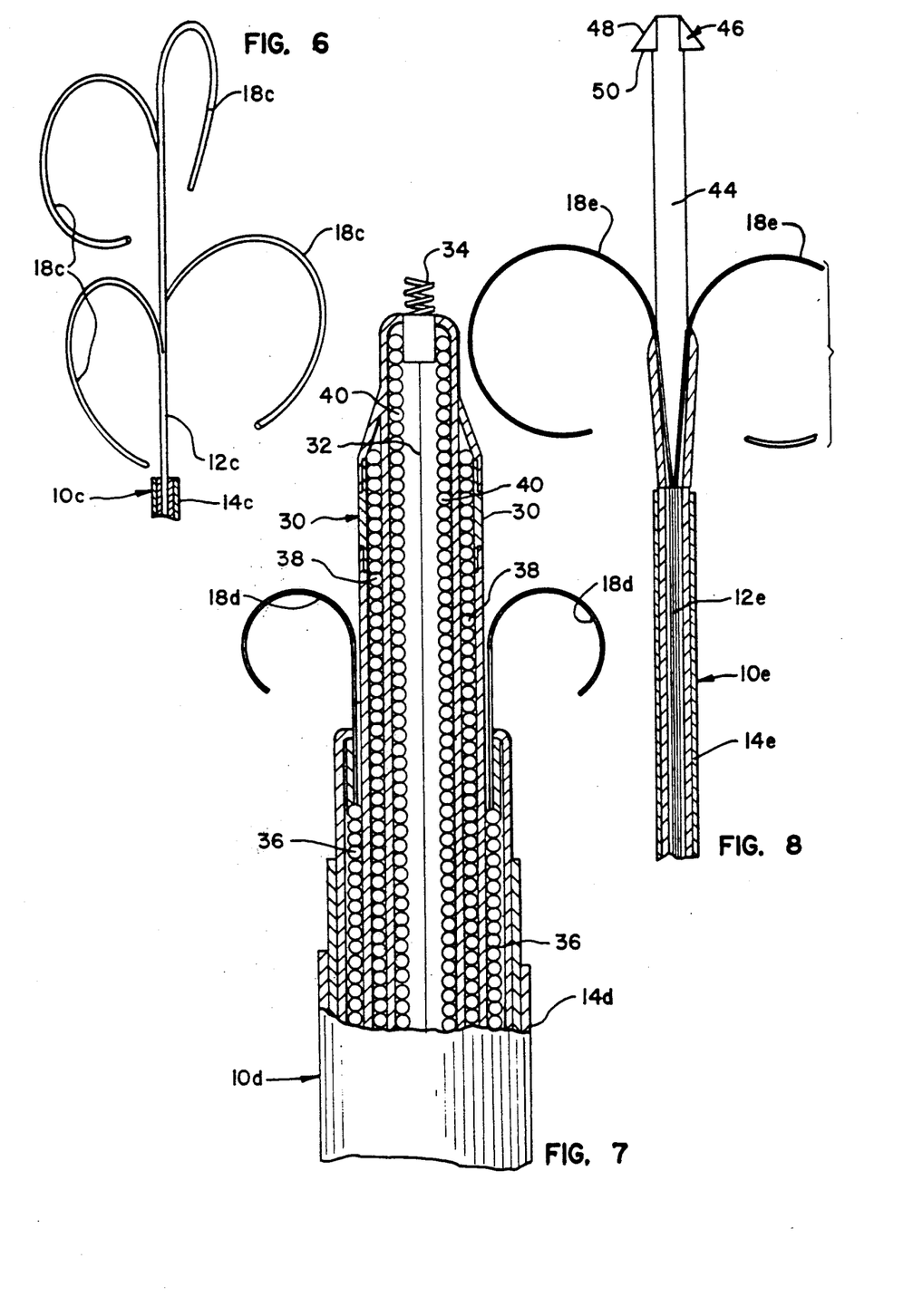
FIGS. 6 through 8 are each plan views, taken partly in section, of additional, separate embodiments of the multiple electrode defibrillator lead of this invention.

Turning to FIG. 6, another defibrillator lead 10c is shown at its distal end, in its natural, expanded configuration.

Lead 10c comprises a conductive lead member 12c and a flexible sheath 14c in a manner similar to the previous embodiments. However, in this embodiment, the respective curvilinear electrodes 18c are staggered in a three dimensional array, which helps with fixation, and which can also serve to reduce tangling of the respective electrodes as they expand outwardly. In other words, one of the electrodes 18c, in reality, would extend upwardly out of the plane of the drawing of FIG. 6. One of the electrodes 18c would extend downwardly out of the plane. Other of the electrodes 18c could remain substantially adjacent to the plane, extending right and left therealong, to define a three dimensional array of curvilinear electrodes.

Because of the three dimensional arrangement, of the electrodes in FIG. 6, they are more likely to contact cardiac tissues when used endocardially. When used intrapericardially or extrapericardially, the three dimensional configuration will create friction forces on the heart to wedge the lead in place, thereby stabilizing it. Contrariwise, the electrodes 18, 18b of FIGS. 1 and 5 are in opposed relation to each other, but they are shown to all substantially occupy a single plane.

Referring to the embodiment of FIG. 7, a more complex lead 10d is disclosed. The electrode assembly at its distal tip comprises a sensing electrode component 30 for sensing heart action. curvilinear defibrillator electrodes 18d are provided in a manner similar to previous embodiments. Likewise, a central lumen 32 is provided to receive a stylet for straightening and stiffening if desired.

Outer sheath 14d is also provided for straightening defibrillation electrodes 18d, and then for allowing them to be deployed upon retraction of sheath 14d, as shown in FIG. 7.

Additionally, at the distal tip, a screw-in pacing electrode/fixation device 34 is disclosed, this device being known per se in the prior art.

Various conductor coals are provided in coaxial relation with each other to provide electrical communication with the respective electrodes. Conductor coil 36 communicates with defibrillator electrodes 18d. Conductor coil 38 communicates with sensing electrode 30. Conductor coil 40 communicates with pacing electrode 34, which pacing electrode also serves as a fixation device, since it can screw into the heart tissue for retention therein.

Thus, the lead of FIG. 7 is capable of sensing heart action, pacing the heart, and defibrillating.

Referring to FIG. 8, another embodiment 10e of the deployable lead of this invention is disclosed. In this embodiment, lead body 12e may comprise a cable of wound or otherwise bonded-together, separate conductors, which diverge outwardly at their distal ends to form the respective defibrillator electrodes 18e. Sheath 14e may initially overlie defibrillator electrodes 18e in the manner previously described. Then, when the electrodes are advanced to their proper position, sheath 14e may be retracted to allow the lateral curvilinear expansion of electrodes 18e as shown.

Lead extension 44 is disclosed, being bonded to the diverging strands of lead cable 12e. At the distal end of lead extension 44, lead retainer means 46 may be provided, being a plurality of radially extending vanes 48, intended for entanglement with the trabeculae of the heart interior, since the distal edges of vanes 48 are tapered, and the proximal edges 50 are not, lead 10e can typically be readily advanced into the ventricle of the heart, so that the lead becomes affixed in position and then can be withdrawn only with difficulty.

Figure 9:
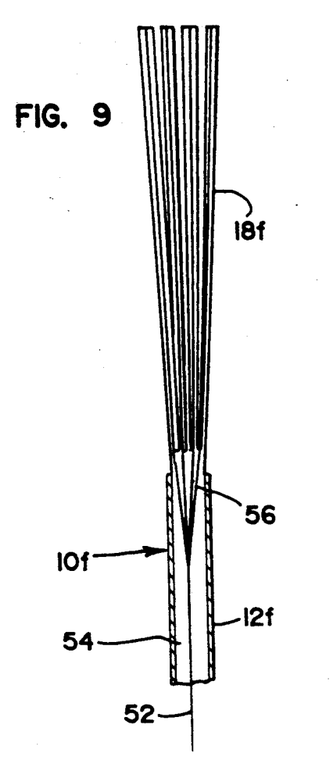
FIG. 9 is a plan view, taken partly in section, of a multiple electrode defibrillator lead of this invention which is straightened into a travelling position by means of an internal stylet having multiple distal branches.
Figures 10, 11:
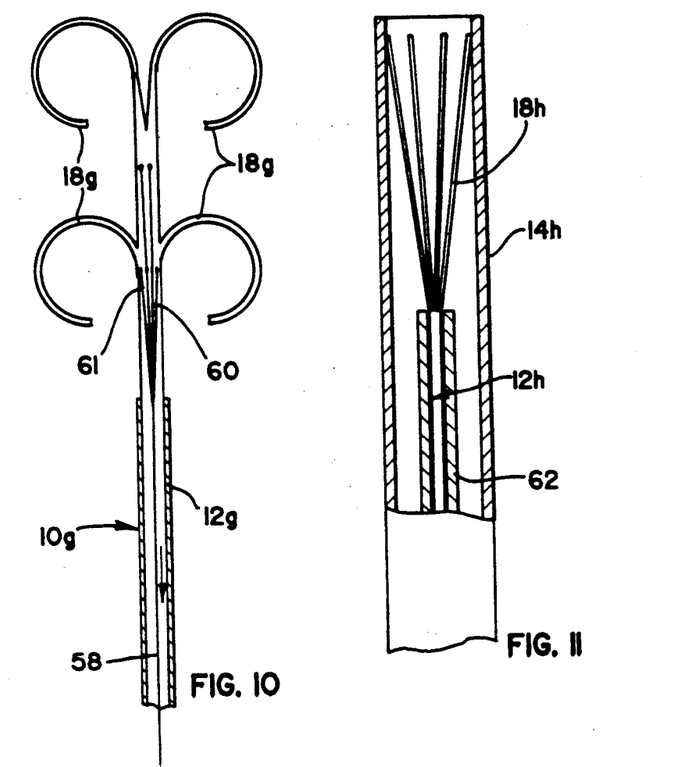
FIG. 10 is a plan view, taken partly in section, of a modified lead similar to that of FIG. 9 after the stylet has been withdrawn from the multiple electrodes.
FIG. 11 is a plan view, taken partly in section, showing another embodiment of the lead of this invention.

Referring to FIGS. 9 and 10, lead 10f comprises a lead body 12f made typically of a coil of conductive metal as in previous embodiments. However, at the distal end of lead body 12f, the lead body divides into a plurality of branching electrodes 18f made of wire coils. A compound stylet 52 is provided which extends through the lumen 54 of lead body 12f. Stylet 52 branches into a series of stylet branches 56, each of which branches extends into the coiled wire electrodes 18f, holding them in straight configuration as shown in FIG. 9.

Then, after implantation, lead body 52 can be pulled proximally, to cause the respective curvilinear electrodes to deploy by flexing laterally outwardly toward their natural, curved arrangement.

FIG. 10 shows a modification of FIG. 9 in which lead body 10g defines four curvilinear electrodes 18g which branch off from the lead body at two different areas rather than all branching off in a single area as in FIG. 9.

Compound stylet 58 is similar in design to stylet 52 of the previous embodiment, except that two of the branching stylet portions 60 are longer than other branching portions 61. Thus, in the original configuration, the stylet 58 in advanced position can hold curvilinear electrodes 18g in a configuration which is generally straight and parallel to the axis of the lead 10g. Then, when stylet 58 is withdrawn as shown in FIG. 10, the respective curvilinear electrodes 18g deploy outwardly in a curved arrangement from the remainder of the lead, as shown.

Referring to FIG. 11, defibrillator lead 10h shows a lead body 12h which terminates, as before, at its distal end in a series of branching electrodes 18h.

An inner stiffening catheter 62 may be provided, while outer sheath 14h is also provided to hold the respective electrodes in a generally longitudinal and straight configuration. This can be used in a situation where the lead body 12h is very flexible, and thus requires stiffening for advancement.

Then, upon emplacement, both sheath 10h and stiffening catheter 62 may be withdrawn, if desired, while the respective curvilinear electrodes 18h deflect outwardly into the desired, curved arrangement.

FIG. 12 shows the installation of a pair of leads in accordance with this invention on and in the heart. Lead 64 is shown to enter the right ventricle through the venous system. Electrodes 18 of lead 64 lie on the endocardium of the right ventricle, being in their second position, extending laterally outwardly from the lead in a curved arrangement. Alternatively, the electrodes 18 of lead 64 may be positioned to lie within the pericardial cavity or on the outer surface of the parietal pericardium.

A second lead 70 is shown to penetrate the parietal pericardium 68 through a second aperture 72, to cause its electrodes 18 to lie on the epicardium of the left ventricle. Alternatively, the curvilinear electrodes 18 of lead 70 may be positioned on the outer surface of the parietal pericardium 68, rather than being positioned between the parietal pericardium 68 and the epicardium.

Figure 13:
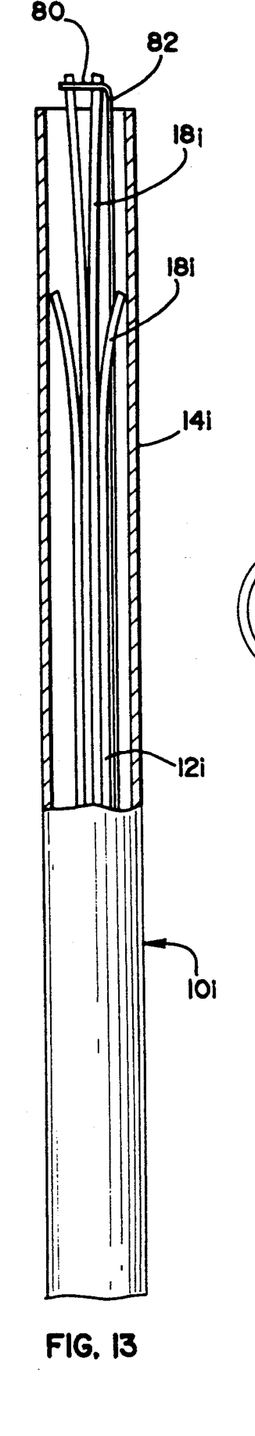
FIG. 13 is a plan view, taken partly in section, showing yet another embodiment of the lead of this invention, in its retracted configuration.
Figures 14, 15:
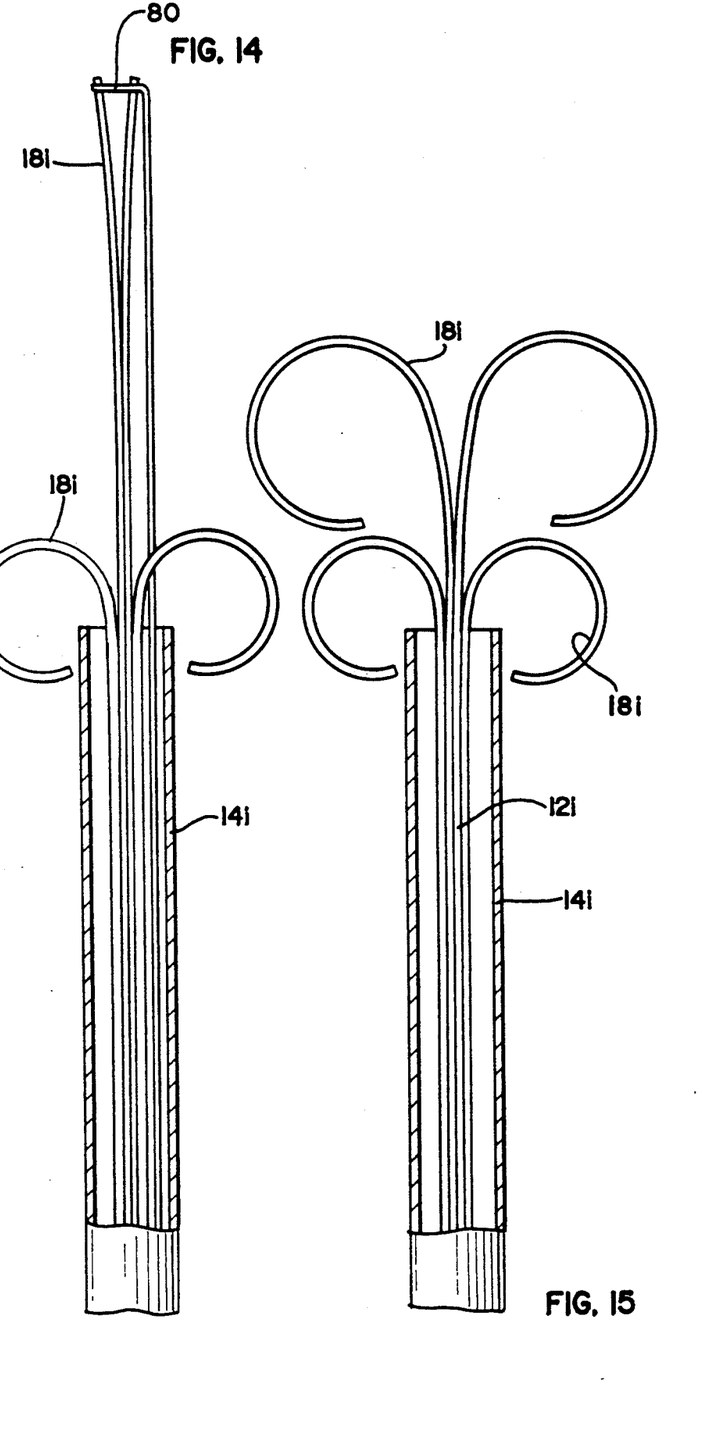
FIG. 14 is a plan view, taken partly in section, of the lead of FIG. 13 shown in its advanced configuration in which some of the curvilinear electrodes are deployed outwardly.
FIG. 15 is a view similar to that of FIG. 14 in which all of the curvilinear electrodes have deployed outwardly in their advanced position.

Referring to FIGS. 13 through 15, another embodiment of the defibrillator lead of this invention is disclosed. As before, lead 10i defines an inner flexible, conductive lead member 12i terminating at its distal end into a plurality of separate, curvilinear electrodes 18i, some of which are longer than the other. Sheath 14i is also provided, being advanceable and retractable as in the previous embodiments, and for a similar purpose.

Also, the longer curvilinear electrodes 18i are retained at their distal ends by a wire loop 80, which is carried by a stylet 82 that extends through the length of defibrillator lead 10i.

In use, defibrillator lead 10i is advanced through the patient to its desired position while occupying the sliding position of FIG. 13 with respect to sheath 14i. Then, when the lead is properly positioned, sheath 14i may be retracted as illustrated in FIG. 14. This causes the shorter curvilinear electrodes 18i to deploy laterally outwardly as shown. However, the longer curvilinear electrodes 18i do not deploy outwardly because they are retained in their straightened position by loop 80. Then, the user, from the proximal end of the defibrillator lead, advances or retracts stylet 82 cause loop 80 to be moved out of its engaging relation with the longer curvilinear electrodes, and optionally removed. Accordingly, the defibrillator lead electrodes all naturally deploy laterally outwardly to the desired position, as shown particularly in FIG. 15.

Thus, a multiple electrode deployable lead is provided, exhibiting substantial advantages over prior art leads, and being particularly suitable for defibrillation, but also potentially useful for other functions such as pacing and sensing of heart action.

The above has been offered for illustrative purposes only, and is not intended to limit the scope of the invention of this application,, which is as defined in the claims below.

That which is claimed is:

1. An implantable defibrillator lead which comprises: a flexible, conductive lead member having proximal and distal and portions; a sheath enclosing said lead member in longitudinally slidable relation, whereby a distal end portion of said lead member is enclosed in said sheath in a first sliding position, and said distal end portion projects from the distal end of said sheath in a second sliding position, said distal end portion defining a plurality of separate, curvilinear defibrillation electrodes which straighten to fit into said sheath in the first position, and which deploy laterally outwardly in a curved arrangement from the remainder of said lead in the second position, said electrodes each comprising a coiled metal wire having an axis extending in a curvilinear direction.

2. The lead of claim 1 wherein the electrodes are made of multifilar coil.

3. The lead of claim 1 wherein each electrode is made of coaxial inner and outer coils, the inner coil being for shape memory and mechanical strength and the outer coil for corrosion resistance.

4. The lead of claim 1 in which said sheath comprises an electrically insulating material.

5. The lead of claim 1 in which said curvilinear electrodes comprise a platinum-iridium alloy.

6. The lead of claim 1 wherein said electrodes comprise essentially 35 weight percent nickel, weight percent cobalt, 20 weight percent chromium and weight percent molybdenum.

7. The lead of claim 1 wherein each electrode has a retaining member running along its length to keep the electrode intact in case of breakage.

8. The lead of claim 1 wherein the electrodes are covered with a corrosion resisting material.

9. The lead of claim 8 wherein the corrosion resisting material is iridium oxide.

10. The lead of claim 1 further comprising a fixation device adjacent the distal end portion.

11. The lead of claim 10 with a screw-in distal end portion for fixation.

12. The lead of claim 10 having a distal end portion with a passive fixation device intended to be caught on trabeculae to hold the lead in place.

13. The lead of claim 1 further comprising a pacing/sensing unit on the distal end portion thereof.

14. The lead of claim 1 wherein the conductive lead member is a multistrandable.

15. The lead of claim 1 wherein the lead is held in position using an inner stylet.

16. The lead of claim 1 wherein the electrodes extend in different planes to help with fixation and to increase endocardial surface contact when used inside the heart.

17. An implantation defibrillator lead which comprises:
a flexible, conductive lead member having proximal and distal end portions; a sheath enclosing said lead member ion longitudinally slidable relation, whereby a distal end portion of said lead member is enclosed in said sheath in a first sliding position, and said distal end portion projects from the distal end of said sheath in a second sliding position, said distal end portion defining a plurality of separate, curvilinear defibrillation electrodes which straighten to fit into said sheath in the first position, and which deploy laterally outwardly in a curved arrangement from the remainder of said lead in the second position, said curvilinear electrodes comprising coiled wire conductors which are free of a central member extending through said coiled wire.

18. An implantable defibrillator lead which comprises:
a flexible, conductive lead member having proximal and distal end portions; a sheath enclosing said lead member in longitudinallyslidable relation, whereby a distal end portion of said lead member is enclosed in said sheath in a first leading position, and said distal end portion projects from the distal end of said sheath in a second sliding position, said distal end portion defining a plurality of separate, curvilinear defibrillation electrodes which straighten to fit into said sheath in the first position, and which deploy laterally outwardly in a curved arrangement from the remainder of said lead in the second position, said electrodes being staggered in the same plane to distribute current and avoid tangling.

19. An implantable defibrillator lead which comprises:
a flexible, conductive lead member having proximal and distal end portions; a sheath enclosing said lead member in longitudinally slidable relation, whereby a distal end portion of said lead member is enclosed in said sheath in a first sliding position, and said distal end portion projects from the distal end of said sheath in a second sliding position, said distal end portion defining a plurality of separate, curvilinear defibrillation electrodes which straighten to fit into said sheath in the first position, and which deploy laterally outwardly in a curved arrangement from the remainder of said lead in the second position, at least one of the electrodes carrying a removable inner stylet for further straightening.

20. An implantable defibrillator lead which comprises:
a flexible, conductive lead member having proximal and distal end portions; a sheath enclosing said lead member in longitudinally slidable relation, whereby a distal end portion of said lead member is enclosed in said sheath in a first sliding position and said distal end portion projects from the distal end of said sheath in a second sliding position, said distal end portion defining a plurality of separate, curvilinear defibrillation electrodes which straighten to fit into said sheath in the first position, and which deploy laterally outwardly in a curved arrangement from the remainder of said lead in the second position, said lead being held in position using a removable stiffening catheter placed between the lead nd the electrode sheath 21. An implantable defibrillator lead which comprises:
a flexible, conductive lead member having proximal and distal end portions; a sheath enclosing said lead member in longitudinally slidable relation, whereby a distal end portion of said lead member is enclosed in said sheath in a first sliding position, and said distal end portion projects from the distal end of said sheath in a second sliding position, said distal end portion defining a plurality of separate, curvilinear defibrillation electrodes which straighten to fit into said sheath in the first position, and which deploy laterally outwardly in a curved arrangement from the remainder of said lead in the second position, said curvilinear electrodes each defining a spiral shape and connecting to a conductor in said lead at an inner end of said spiral shape.

22. An implantable defibrillator lead which comprises:
a flexible conductive lead member having proximal and distal ends; a flexible sheath having a distal end enclosing said lead member in longitudinally slidable relation, whereby a distal end portion of said lead member is enclosed in said sheath in a first sliding position, and said distal end portion projects from the distal end of said sheath in a second sliding position, said distal end portion defining a Plurality of separate, curvilinear electrodes which straighten to fit into said sheath in the first position, and which extend laterally outwardly in a curved arrangement from the remainder of said lead in the second position, said electrodes comprising a coiled metal wire, free of a central member extending through said coiled wire, having an axis extending in said curvilinear direction.

23. The lead of claim 22 in which at least a pair of said separate, curvilinear electrodes define arcs that project in the second position outwardly in opposed, transverse directions to avoid tangling of said electrodes.

24. The lead of claim 23 in which said separate, curvilinear electrodes h define an arc having an angle of at least about 180° but less than a closed loop.

25. The lead of claim 22 wherein the electrodes are made of multifilar coils.

26. The lead of claim 33 in which at least a pair of said separate curvilinear electrodes define arcs that project in the second position outwardly in opposed transverse directions to avoid tangling of said electrodes.

27. The lead of claim 25 further comprising a fixation device adjacent the distal end portion.

28. The lead of claim 22 wherein each electrode has a retaining member running along its length to keep the electrode intact in case of breakage.

29. The lead of claim 22 wherein the electrodes are staggered in the same plane to distribute current and avoid tangling.

30. The lead of claim 22 wherein the electrodes extend in different planes to help with fixation and to increase endocardial surface contact when used inside the heart.

31. The lead of claim 22 further comprising at least one straight element in the region of the electrodes to be used as an additional electrode element or to provide an adjacent lumen.

32. An implantable defibrillator lead which comprises:
a flexible, conductive lead member having proximal and distal end portions; said distal end portion defining a plurality of separate, curvilinear electrodes, said lead member defining a central lumen, and said separate, curvilinear electrodes each defining branch lumens that communicate with said central lumen, said electrodes in a natural, unstressed configuration extending laterally outwardly in a curved arrangement form the remainder of said lead; stylet means extending through the lumen of said lead member, said stylet means defining attached, distally positioned branch stylets, said branch stylets extending through branch lumens of said curvilinear electrodes to straighten said electrodes, whereby said defibrillator lead may be placed in a patient while said electrodes are in straightened condition due to the presence of said branch stylets, and said electrodes may assume a position approximating said natural, unstressed configuration when the stylet means is removed from the branch lumens.

33. The lead of claim 32 in which said separate, curvilinear electrodes each define an arc having an angle of at least about 180° but less than a closed loop.

* * * * *

UNITED STATES PATENT AND TRADEMARK OFFICE
CERTIFICATE OF CORRECTION

PATENT NO. : 5,282,845

DATED : FEBRUARY 1, 1994

INVENTOR(S) : MARY E. BUSH, ET AL

It is certified that error appears on the above-identified patent and that said Letters Patent is hereby corrected as shown below:

Col. 10, Claim 6, Lines 52-53 "weight percent cobalt" should be "35 weight percent cobalt"
Col. 10, Claim 6, Lines 53-54 "weight percent molybdenum" should be "10 weight percent molybdenum"
Col. 11, Claim 14, Line 4 "multistrandable" should be "multistrand cable"
Col. 11, Claim 17, Line 10 "implantation" should be "implantable"
Col. 11, Claim 17, Line 14 "member ion" should be "member in"
Col. 11, Claim 18, Line 34 "first leading" should be "first sliding"
Col. 12, Claim 20, Line 9 "lead nd" should be "lead and"
Col. 12, Claim 24, Line 51 "electrodes h" should be "electrodes each"
Col. 13, Claim 32, Line 17 "arrangement form" should be "arrangement from"

Signed and Sealed this

Tenth Day of October, 1995

Attest:

BRUCE LEHMAN

*Attesting Officer*        *Commissioner of Patents and Trademarks*